(12) United States Patent
Ina et al.

(10) Patent No.: US 6,636,303 B2
(45) Date of Patent: Oct. 21, 2003

(54) FOREIGN SUBSTANCE INSPECTING METHOD AND APPARATUS, WHICH DETECT A HEIGHT OF A FOREIGN SUBSTANCE, AND AN EXPOSURE APPARATUS USING THIS INSPECTING APPARATUS

(75) Inventors: Hideki Ina, Kanagawa (JP); Koichi Sentoku, Tochigi (JP); Takahiro Matsumoto, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/822,338

(22) Filed: Apr. 2, 2001

(65) Prior Publication Data

US 2001/0043326 A1 Nov. 22, 2001

(30) Foreign Application Priority Data

Apr. 5, 2000 (JP) ......................................... 2000-103369

(51) Int. Cl.⁷ ............................................... G01N 21/00
(52) U.S. Cl. ............................... 356/237.3; 356/237.5; 356/612; 250/559.4
(58) Field of Search ........................... 356/237.1, 237.2, 356/237.3, 237.4, 237.5, 601, 612, 614, 394; 250/559.4, 559.41, 559.42, 559.45

(56) References Cited

U.S. PATENT DOCUMENTS

| | | | |
|---|---|---|---|
| 4,342,515 A | * 8/1982 | Akiba et al. | 356/237.1 |
| 4,676,637 A | * 6/1987 | Uto et al. | 356/237.1 |
| 4,834,540 A | 5/1989 | Totsuka et al. | 356/401 |
| 4,861,162 A | 8/1989 | Ina | 356/401 |
| 4,886,974 A | 12/1989 | Ina | 250/561 |
| 4,952,058 A | * 8/1990 | Noguchi et al. | 356/237.1 |
| 5,278,635 A | * 1/1994 | Ono et al. | 356/430 |
| 5,309,197 A | 5/1994 | Mori et al. | 355/53 |
| 5,323,207 A | 6/1994 | Ina | 355/53 |
| 5,369,486 A | 11/1994 | Matsumoto et al. | 356/349 |
| 5,410,400 A | * 4/1995 | Shishido et al. | 356/237.4 |
| 5,717,485 A | * 2/1998 | Ito et al. | 356/237.1 |
| 5,751,426 A | 5/1998 | Nose et al. | 356/356 |
| 6,154,281 A | 11/2000 | Sentoku et al. | 356/401 |
| 6,292,260 B1 | * 9/2001 | Lin et al. | 356/237.4 |

* cited by examiner

Primary Examiner—Huy Mai
(74) Attorney, Agent, or Firm—Fitzpatrick, Cella, Harper & Scinto

(57) ABSTRACT

A foreign substance inspecting method includes the steps of detecting a height of a foreign substance attaching to a periphery of a wafer by irradiating a light beam from a light source to the wafer, thereby detecting the presence/absence of a foreign substance with not less than a predetermined height. The predetermined height is set to be substantially equal to a gap between the wafer and a mask at a wafer exposure.

13 Claims, 15 Drawing Sheets

FOREIGN SUBSTANCE INSPECTING METHOD AND APPARATUS, WHICH DETECT A HEIGHT OF A FOREIGN SUBSTANCE, AND AN EXPOSURE APPARATUS USING THIS INSPECTING APPARATUS

FIELD OF THE INVENTION

The present invention relates to a foreign substance inspecting method and apparatus suitably used in lithography (e.g., in Proximity X-ray Lithography: to be referred to as PXL hereinafter) with which a mask pattern is exposed and transferred with a one-to-one exposure onto a wafer arranged close to the mask by using, as a light source, X-rays with a wavelength of 7 Å to 10 Å and output from an electron storage ring (to be referred to as an SR hereinafter) serving as a synchrotron radiator, and an exposure apparatus using this inspecting method.

More particularly, the present invention relates to a foreign substance inspecting method and apparatus which cope with the problem of a foreign substance specific to PXL exposure with which exposure is performed by separating a mask and wafer from each other by a very small distance of several tens of $\mu$m or the like, and an exposure apparatus using this inspecting method.

BACKGROUND OF THE INVENTION

PXL is a micropattern exposure technique with which a mask is set to oppose a wafer at a gap of 10 $\mu$m to 30 $\mu$m and a pattern on the mask is transferred to the wafer by Fresnel diffraction.

As a PXL type exposure apparatus, currently, one with a maximum exposure range of 52 mm square is expected to be manufactured. As this exposure apparatus performs one-to-one exposure with the maximum exposure range of 52 mm square, if exposure is to be performed on a wafer with a size of 4 inches or more, the entire surface of the wafer cannot be exposed by one exposure operation. For this reason, exposure is performed while sequentially moving the wafer so that the entire surface of the wafer is exposed, as with a repetitive stepper for an optical exposure apparatus. Hence, a PXL exposure apparatus is sometimes called a one-to-one exposure X-ray stepper.

The characteristic feature of the PXL exposure apparatus resides in its high resolution. With a high resolution of 100 nm or less and alignment of 20 nm or less having already been reported, the PXL exposure apparatus may become a leading exposure method for a 1-GDRAM or RAMs with capacities larger than that. One of the special items of the PXL is an X-ray mask. A conventional manufacturing process for an X-ray mask will be described with reference to FIGS. 9 to 19. Note that in FIGS. 9 to 19, for descriptive convenience, the thicknesses of the films are illustrated with a proportion different from that of actual films.

In fabrication of the X-ray mask, first, as shown in FIG. 9, a Si wafer 30 is prepared as a substrate and, as shown in FIG. 10, a SiC film 31 called a membrane and with a thickness of 2 $\mu$m to 3 $\mu$m is formed on it. When forming the SiC film 31 on the Si wafer 30, SiC films are formed on the upper and lower surfaces and side surfaces of the wafer. As the SiC films on the lower surface and side surfaces of the wafer are not related to the function of the mask, they are omitted in FIG. 10 and so on.

In FIG. 11, the SiC surface is polished to form a planar SiC film 32, and an ITO film or SiO$_2$ film 33 is formed, as shown in FIG. 12. In the step of FIG. 13, an X-ray absorber 34, e.g., W, Ta, or Ta$_4$B, having a relatively high X-ray absorption performance is formed to a thickness of 0.3 $\mu$m to 0.5 $\mu$m. In FIG. 13, preparation of the substrate is completed.

In the step of FIG. 14, a resist is applied to the substrate, and a desired pattern is drawn on the substrate with an electron beam drawing unit. Then, the substrate is subjected to development, etching, and resist removal, thereby forming a pattern. When the pattern is formed, the opposite side to the pattern portion is etched back so X-rays can be transmitted through a Si portion 35 within the exposure range. Finally, in FIG. 16, the substrate is mounted on a frame 36, thus completing an X-ray mask.

In order to decrease drawing errors, the frame 36 in the state shown in FIG. 13 may be mounted as shown in FIG. 17, and Si in the portion 31 within the exposure range may be etched back, so X-rays can be transmitted through this portion. After that, a resist is applied to the substrate, and a desired pattern is drawn on the substrate with an electron beam drawing unit. Then, the substrate is subjected to development, etching, and resist removal, thereby forming a pattern. The X-ray mask shown in FIG. 19 is thus completed. It is known that this method has a high precision since the substrate is finally mounted on the frame.

In fact, however, if the substrate is subjected to the drawing process after it is mounted on the frame, the mount may be peeled due to heat. Therefore, conventionally, the X-ray mask is usually formed with the steps of FIGS. 9 to 16. The frame 36 is sometimes called a support ring, and is made of, e.g., Pyrex or SiC. To mount the membrane, anodic bonding or an adhesive is used. Another method is also proposed in which, as shown in FIG. 17, the frame is also made of Si to form an integral frame 37, and an Si wafer substrate and the frame are formed integrally.

In the PXL exposure apparatus, since a membrane with a thickness of 2 $\mu$m to 3 $\mu$m is used as a mask, it has a specific problem in that a foreign substance with a size equal to or larger than the exposure gap is sandwiched between the wafer and mask (particularly, a SiC membrane) to come into contact with them, thereby fracturing the SiC portion of the mask.

Assuming that a typical exposure gap is 10 $\mu$m, the existence of a foreign substance with a size equal to or larger than 10 $\mu$m between the wafer and mask may seem nonsensical in semiconductor manufacture where the idea of high yield prevails. This size, however, cannot be ignored as the size of a foreign substance occurring on the periphery of a wafer.

Most exposure apparatuses used in present semiconductor manufacture are optical exposure apparatuses, and a foreign substance attaching to the periphery of a wafer does not pose an issue. In an optical exposure apparatus, since the distance between the wafer and the projection optical system of the exposure apparatus is at least 1 cm, the problem of the contact of a foreign substance does not arise, and the situation is completely different from that of the PXL exposure apparatus. Furthermore, since the periphery of the wafer is not used for formation of ICs, an inspection for a foreign substance on the periphery of the wafer is not conventionally performed.

The present inventors performed observation of the peripheries of various types of wafers. It has become apparent that many large-sized foreign substances are present on the periphery of a wafer even in the semiconductor manufacture where the idea of high yield prevails. However, due to the reason described above, a foreign substance on the periphery of a wafer does not pose a serious issue in the conventional optical exposure apparatus. Even in the optical exposure apparatus, a foreign substance can move from the periphery of a wafer and shift onto the wafer pattern, thus causing a problem. As a countermeasure for this, inspection is performed by using a wafer foreign substance inspecting apparatus for detecting a foreign substance on a patterned wafer, so that a decrease in yield is prevented.

Still, in the PXL exposure apparatus, unlike in the optical exposure apparatus, a foreign substance on the periphery of a wafer can cause fracture of a mask. This is a serious problem.

FIGS. 20 to 22 are views for explaining a phenomenon that occurs when a mask 1 is exposed at a predetermined gap with a foreign substance 13 attaching to the periphery of a wafer 2. In FIG. 21, after the wafer moves, when a portion near the periphery of the wafer is exposed, a force acts on the foreign substance 13 attaching to the wafer 2. In the state of FIG. 21, since the foreign substance 13 is in contact with that portion of the mask 1 where the Si portion is not etched back, it does not fracture the mask 1.

After the shot shown in FIG. 21 is exposed, when the wafer 2 is moved so as to expose another portion, a force acts on the foreign substance 13. As shown in FIG. 22, upon movement of the wafer 2, the foreign substance 13 is separated from the wafer 2 and is moved to attach to the SiC portion of the etched-back transfer pattern portion 35 of the mask 1. If exposure and movement of the wafer are repeated in this manner, a force acts on the foreign substance 13 again, and sometimes SiC, with a thickness of 2 $\mu$m to 3 $\mu$m, may be fractured.

A case wherein a foreign substance attaches to the periphery of a wafer has been described. The same phenomenon occurs when a foreign substance attaches to the periphery of a mask. FIGS. 23 and 24 show this case. First, in the initial shot of wafer exposure, the foreign substance 13 attaching to the mask 1 gets sandwiched between the mask 1 and wafer 2, and a force acts on the mask 1. At this time point, the mask 1 is not fractured in the same manner as in the case shown in FIG. 21 wherein a foreign substance attaches to the periphery of a wafer. Subsequently, when the wafer 2 moves, the foreign substance 13 is moved to a SiC portion of the mask 1 where the Si portion is not etched back, and the mask 1 is fractured undesirably, as shown in FIG. 24.

As described above, in the PXL exposure apparatus, a foreign substance attaching to the periphery of a wafer or mask, particularly, a large foreign substance with a size equal to or larger than the exposure gap which does not pose an issue in the optical exposure method, causes mask fracture, and is accordingly a serious problem.

Even if the mask is not fractured, when the foreign substance which has moved to the wafer and attached to it is not detected by another inspection, the original function of the semiconductor cannot be achieved, and a decrease in yield results. Conventionally, however, the possibility of movement of a foreign substance in an optical exposure apparatus is smaller than that in a PXL exposure apparatus, and a foreign substance on the periphery of a wafer is out of interest.

The present invention examined foreign substances on the entire surfaces of a wafer and an X-ray mask, including their peripheries, by using an existing wafer foreign substance inspecting apparatus for inspecting a foreign substance on a patterned wafer. As the existing wafer foreign substance inspecting apparatus, for example, one which illuminates a wafer with polarized light by oblique incidence exists. The detection principle of this method utilizes a feature that a circuit pattern reflects light with the polarization characteristics being maintained, while a foreign substance reflects light in a non-polarized state. This detection system has been manufactured as a product. Such a product has a high throughput with an actual detection time of 1 minute or less with an 8-inch wafer, and accordingly a high reliability, thus contributing to a high yield in semiconductor manufacture.

According to the studies of the present inventors, when the above wafer foreign substance inspecting apparatus is used, a foreign substance on a mask or wafer can be discriminated from a notch in Si in the periphery and can accordingly be detected. Meanwhile, in the vicinity of the periphery of the mask, even when no foreign substance is present, a false signal corresponding to the size of an ordinary foreign substance or larger than that is sometimes generated, and this false signal may be erroneously detected as a large-sized foreign substance.

It is apparent that a false signal is generated because a mask is not conventionally manufactured by paying attention to the structure of is periphery. Various types of foreign substances caused by mask handling exist on the mask periphery, e.g., a foreign substance attaching to the periphery when the wafer is held by a CVD (Chemical Vapor Deposition) unit, variations in thickness of SiC or an absorber due to the influence of the surrounding atmosphere, or film removal occurring as the film is scratched by tweezers when the mask is to be mounted on the frame.

When the X-ray mask is measured with a conventional foreign substance inspecting apparatus for a patterned wafer, typically, a foreign substance like those described above may be determined as being a large-sized foreign substance with a size of 10 $\mu$m or more. The existing wafer foreign substance inspecting apparatus uses a detection principle that a foreign substance scatters light by isotropic scattering, and determines the size of a foreign substance based on a correlation table with respect to signal outputs stored in advance. If the film is peeled or film thickness varies, light is refracted and scattered through a complicated process, so the polarized light rotates. Thus, a large signal output is detected when compared to a case wherein a foreign substance which has the same size as that described above and which causes isotropic scattering is present. For example, when the film is peeled, this may be erroneously determined as being a large-sized foreign substance with a size of 10 $\mu$m or more, which is larger than the actual size.

It is also apparent that, on the wafer periphery, a foreign substance is crushed during transfer or while the wafer is being mounted on a carrier, and a large-sized, but not tall, foreign substance is detected. A peeled film, a nonuniform-thick film, or a flat foreign substance on the wafer, however, is not a foreign substance with a height of 10 $\mu$m or more, which can fracture the mask and must accordingly be solved by the present invention.

SUMMARY OF THE INVENTION

It is an object of the present invention to provide a foreign substance inspecting method and apparatus which can realize exposure in connection with a foreign substance detecting function for discriminating a foreign substance that really poses an issue in a PXL exposure apparatus from a harmless foreign substance, and an exposure apparatus using this inspecting method.

The foreign substance inspecting method and apparatus according to the present invention, and the exposure apparatus using this inspecting method, are devised in order to solve the problem of a foreign substance specific to the PXL described above.

More specifically, the present invention is characterized in that, during exposure which is performed by separating a mask and wafer from each other by a predetermined distance, wafer foreign substance inspection for detecting the surface of the wafer and a foreign substance simultaneously, thereby detecting whether or not a foreign substance with a height equal to a preset value or more is present, is performed in a PXL exposure apparatus, a coater/developer, or the like.

For example, the wafer foreign substance inspecting apparatus can employ a method with which the periphery of a wafer is irradiated with light in a direction almost tangent to the outer circumference of the wafer, then the irradiation light is reflected and returned to an optical path it has passed along in order to irradiate the periphery of the wafer again, and the irradiating light is received.

Conventionally, an existing foreign substance inspecting apparatus for a patterned wafer determines the size of a foreign substance based on a detection signal and a correlation table showing the relationship between a prestored signal output and a foreign substance. In other words, the size of a foreign substance is merely determined from the magnitude of a signal output, thereby measuring the size of the foreign substance. To detect a foreign substance that might fracture a mask, the height of the foreign matter, which is the most significant parameter, is not detected. Accordingly, to simply apply the conventional foreign substance inspecting apparatus, which detects the size of a foreign substance from a signal output, to a PXL exposure apparatus is not sufficient. This problem can be solved only when the height of the foreign substance is detected directly.

In a wafer foreign substance inspecting method and apparatus according to the present invention, and an exposure apparatus using this inspecting method, a foreign substance inspecting apparatus, using a detection method capable of detecting the height of a foreign substance on the periphery of a wafer in question with a high throughput, is prepared. This foreign substance inspecting apparatus is applied to a PXL exposure apparatus, so the problem of foreign substance specific to the PXL is solved.

More specifically, with a foreign substance inspecting method according to the present invention, a height of a foreign substance attaching to a periphery of a wafer is detected, thereby detecting the presence/absence of a foreign substance with not less than a predetermined height.

The foreign substance inspecting method according to the present invention is applied to an exposure apparatus that exposes a mask and wafer separated from each other at a predetermined distance, thereby detecting a height of a foreign substance attaching to the wafer.

The foreign substance inspecting method according to the present invention is applied to an exposure apparatus that exposes a mask and wafer separated from each other at a predetermined distance, thereby detecting a size and height of a foreign substance attaching to the wafer.

A foreign substance inspecting apparatus inspecting a foreign substance apparatus attaching to a wafer according to the present invention comprises an irradiation unit for irradiating a periphery of the wafer with light in a direction substantially tangent to an outer circumference of the wafer while rotating the wafer, and a detection unit for detecting the presence/absence of a foreign substance with not less than a predetermined height on the basis of the irradiating light.

An exposure apparatus according to the present invention exposes a mask and wafer separated from each other at a predetermined distance, and comprises a foreign substance inspecting apparatus having an irradiation unit for irradiating a periphery of a wafer with light in a direction substantially tangent to an outer circumference of the wafer while rotating the wafer, and a detection unit for detecting the presence/absence of a foreign substance with not less than a predetermined height on the basis of the irradiating light.

Other objects and advantages besides those discussed above shall be apparent to those skilled in the art from the description of a preferred embodiment of the invention which follows. In the description, reference is made to accompanying drawings, which form a part thereof, and which illustrate an example of the invention. Such an example, however, is not exhaustive of the various embodiments of the invention, and, therefore, reference is made to the claims which follow the description for determining the scope of the invention.

DETAILED DESCRIPTION OF THE PREFERRED EMBODIMENTS

A wafer foreign substance inspecting method and apparatus according to the preferred embodiments of the present invention, and a PXL exposure apparatus and method using this inspecting method will be described in detail with reference to FIG. 1 and so on.

Figure 1:
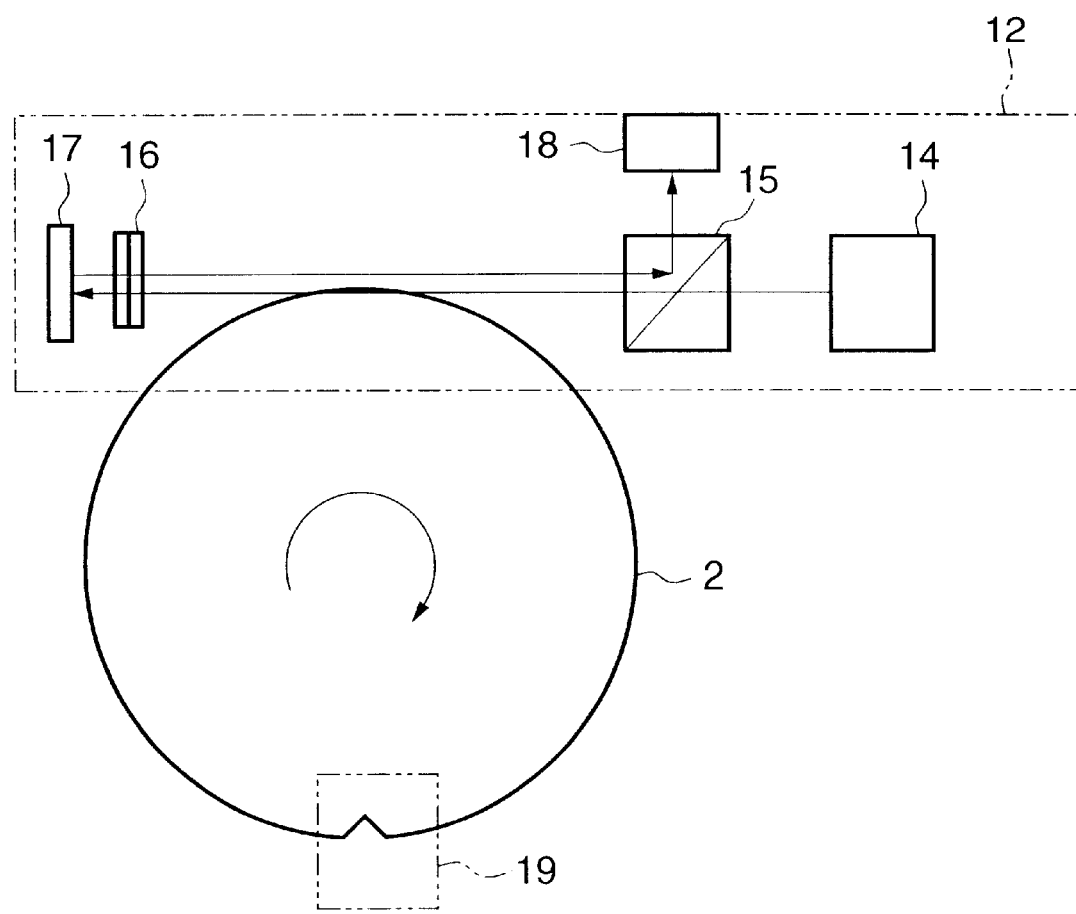
FIG. 1 is a view showing the principle of a foreign substance inspecting apparatus for detecting the height of a foreign substance according to the embodiment of the present invention.

FIG. 1 shows a wafer foreign substance inspecting apparatus according to an embodiment of the present invention.

A wafer 2 to be inspected is arranged on a stage rotatable through 360°, and its outer periphery is measured by a notch detection system 19. The characteristic feature of this embodiment resides in that the wafer 2 is rotated for the purpose of notch detection, and that a foreign substance inspecting apparatus 12 detects the height of a foreign substance on the periphery of the wafer 2.

In the foreign substance inspecting apparatus 12, a beam generated by a semiconductor laser (to be referred to as an LD hereinafter) 14 serving as a light source is collimated by a lens to form parallel light, so the periphery of the wafer 2 to be inspected is irradiated with the parallel light. The irradiating beam is parallel to the direction of a tangent to the outer circumference of the wafer 2, and becomes incident as the parallel light on a position separate from the pattern surface by a predetermined amount to include variations in thickness of the wafer and an error in rotation. For example, if the exposure gap is 20 μm, since a substance of 15 μm or more must be detected, this predetermined amount is 15 μm.

In the arrangement of FIG. 1, light emerging from the LD 14 is collimated to pass through a polarizing beam splitter 15. The passing light is directly transmitted while irradiating a portion above the surface of the wafer, and forms circularly polarized light through a λ/4 plate 16. Polarization by the LD 14 is set in the direction of linear polarization so the polarized light can be transmitted through the polarizing beam splitter 15 easily. Successively, the beam reflected by a mirror 17 is transmitted through the λ/4 plate 16 again to form linearly polarized light. This light irradiates the portion above the surface of the wafer 2, is reflected by the polarizing beam splitter 15 this time, and is guided onto an image sensing element 18. The image sensing element 18 photoelectrically converts the incident beam and outputs an electrical signal.

Although the intensity distribution of the light quantity of the LD 14 is actually a normal distribution, it will be described as being a normal distribution first, and then a calculation method with a strength of the actual normal distribution will be described.

Figure 2:
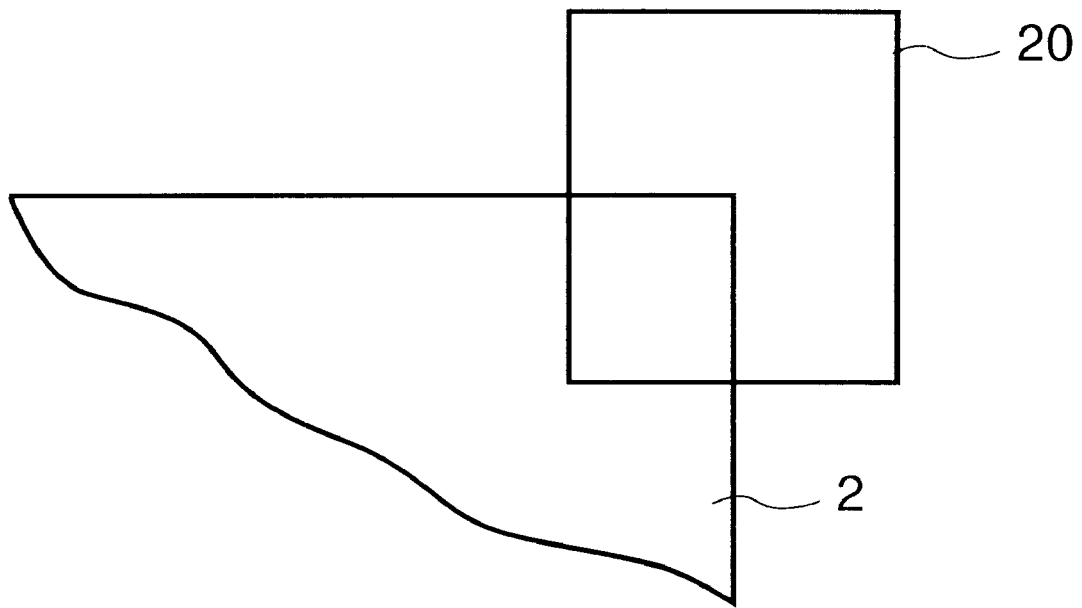
FIG. 2 is a view showing the relationship between a wafer and an irradiation range of the foreign substance detecting apparatus shown in FIG. 1.

FIG. 2 shows the relationship between an irradiation range 20 and the outer periphery of the wafer when the arrangement of FIG. 1 is seen from the light source. The irradiation range 20 has a rectangular shape and is irradiated with a uniform intensity such that the vertex of the surface of the outer periphery of the wafer 2 is the center of irradiation.

Figure 3:
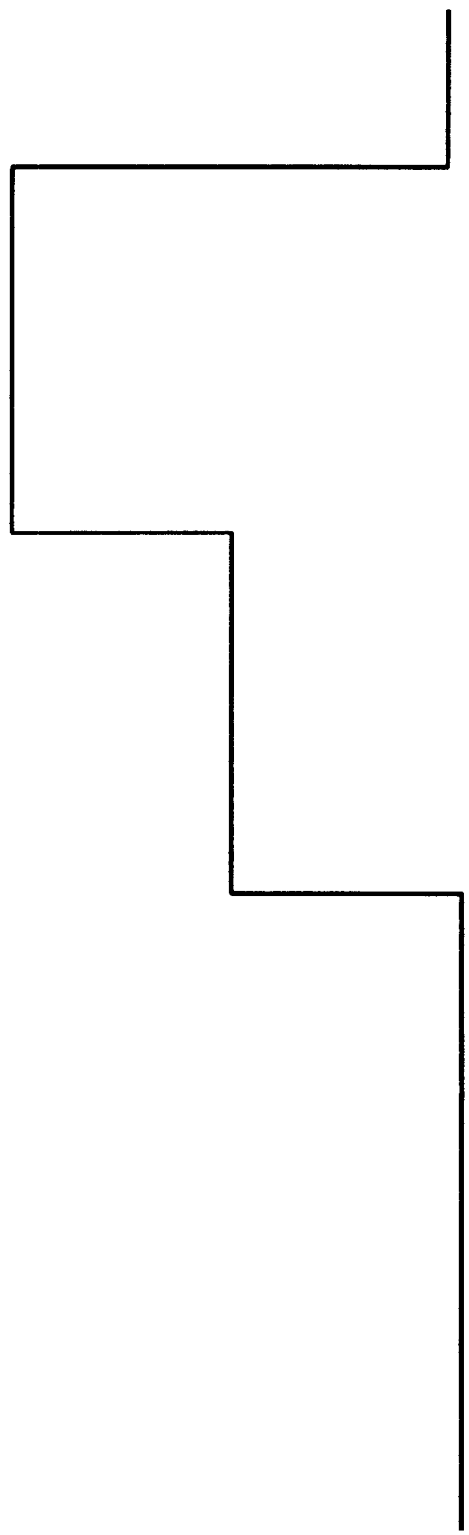
FIG. 3 is a graph showing a signal output obtained with the foreign substance inspecting apparatus when no foreign substance is present on the periphery of the wafer.

FIG. 3 shows a signal output from the image sensing element 18, obtained when no foreign substance is present, such that the direction of height coincides with that of FIG. 2. The surface position of the wafer is recognized from this signal. Within a predetermined region above the pattern surface, the signal intensity is uniform and has no difference. Hence, it can be determined that a foreign substance with a height larger than the predetermined amount is not present.

Figure 4:
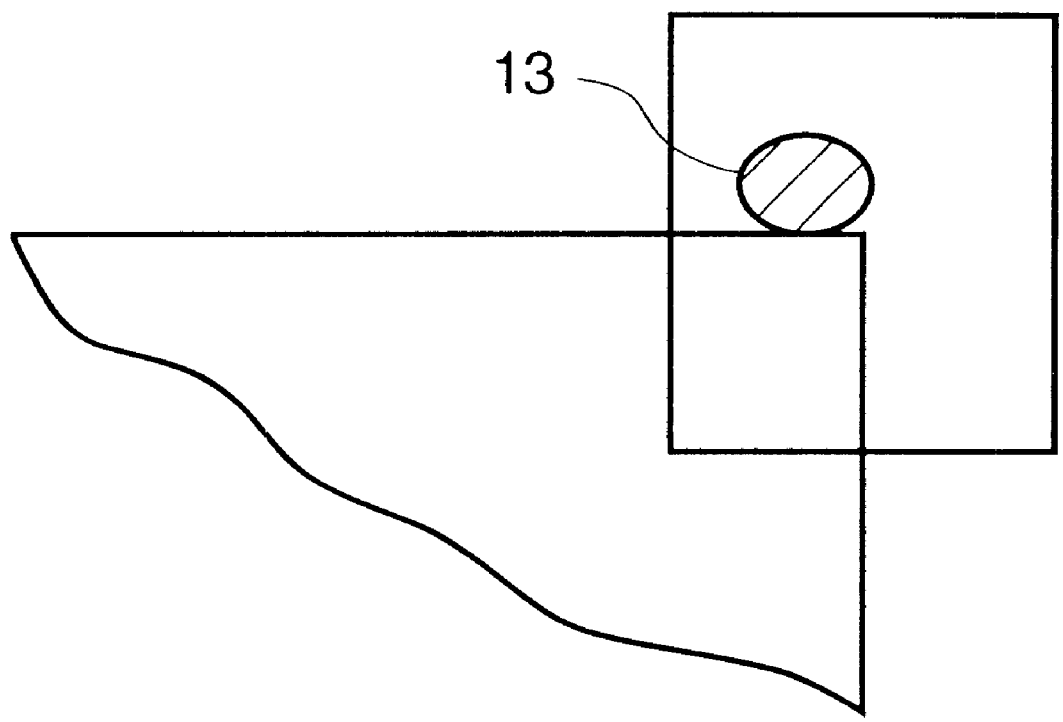
FIG. 4 is a view showing a state wherein a foreign substance is present on the periphery of the wafer.
Figure 5:
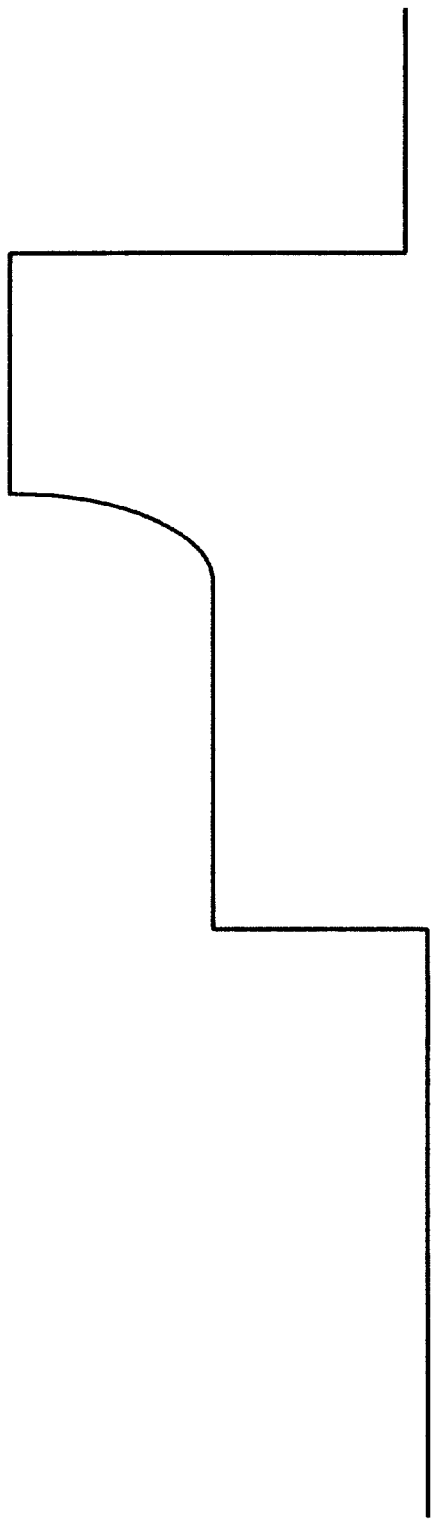
FIG. 5 is a graph showing a signal output obtained in the case of FIG. 4 wherein a foreign substance is present on the periphery of the wafer.

When a tall foreign substance 13 is present as shown in FIG. 4, the signal output from the image sensing element 18 is as shown in FIG. 5 (the direction of height coincides with that of FIG. 4). The signal strength changes even outside the predetermined region above the pattern surface. Hence, it can be determined that a foreign substance with a height larger than the predetermined amount is present. As the exposure gap changes depending on the situation, the height of a foreign substance to be detected can be altered by processing the output from the image sensing element.

The principle of the arrangement of this foreign substance inspecting apparatus utilizes the fact that an inspecting light source wavelength is transmitted through a foreign substance with a low transmittance. In terms of the optical path, as the foreign substance is irradiated twice, the transmittance of the foreign substance is squared, thereby obtaining a signal with a high SN ratio.

Figure 6:
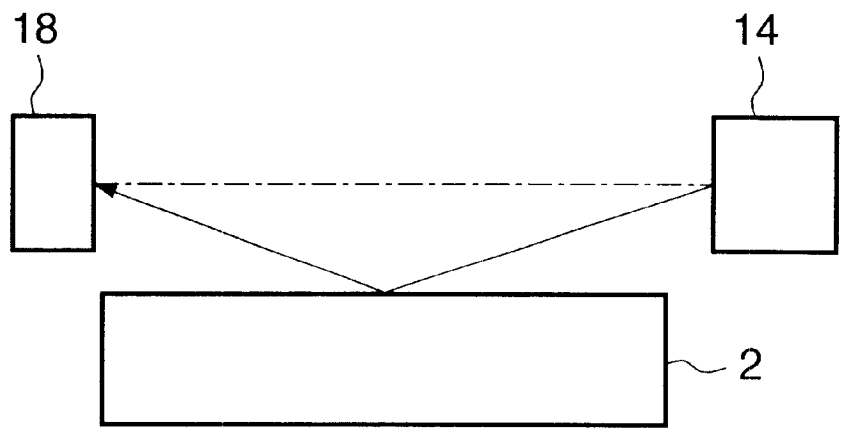
FIG. 6 is a view showing a light beam reflected by a wafer surface in the foreign substance inspecting apparatus according to the embodiment of the present invention.
Figure 7:
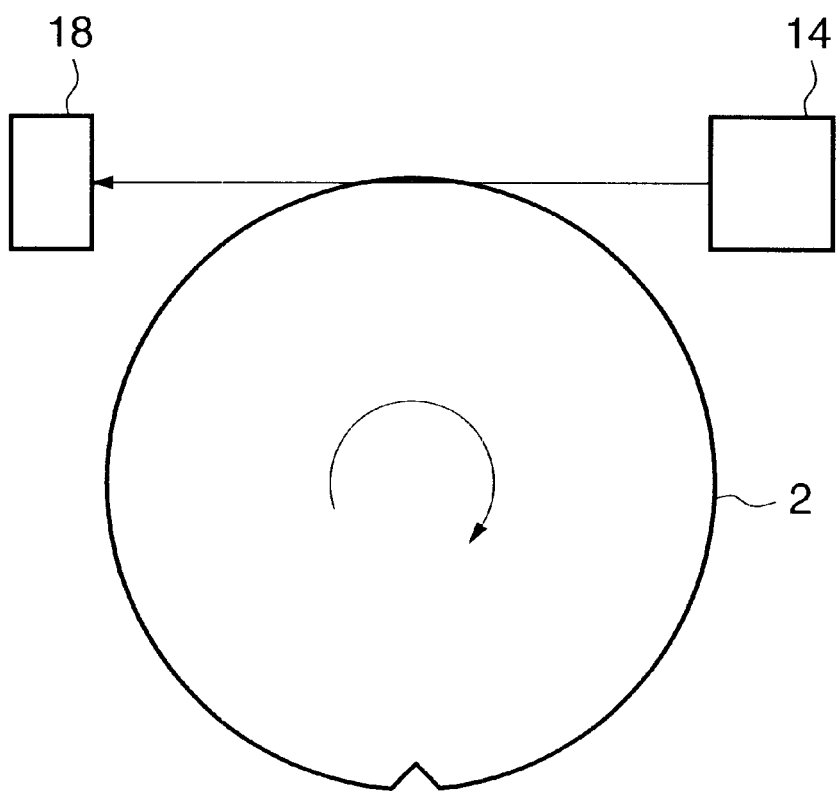
FIG. 7 is a view showing a modification wherein foreign substance inspection is performed without bending X-rays.

According to this foreign substance inspecting apparatus, since the wafer is irradiated twice by reflection, unwanted light can be cut with a compact arrangement. In the arrangement of the optical system, collimated light performs irradiation, as described above. In practice, the divergent light cannot be set completely parallel, and some divergent angle remains in the light. When the divergent light is regularly reflected by the surface of the wafer 2 as shown in FIG. 6, it forms flare light components. Alternatively, the foreign substance may be detected with one irradiation optical path, as shown in FIG. 7. In this case, the distance between the wafer 2 and image sensing element 18 must be increased in order to avoid regular reflected light. If the wafer 2 is irradiated twice as in FIG. 1, the distance between the wafer 2 and image sensing element 18 can be reduced to half, and the apparatus can accordingly be made compact.

When the wafer is rotated through 360° in the foreign substance inspecting apparatus having the above detection principle, the periphery of the wafer can be inspected entirely.

A case of a normal intensity distribution that the actual LD 14 has will be described.

Figure 25:
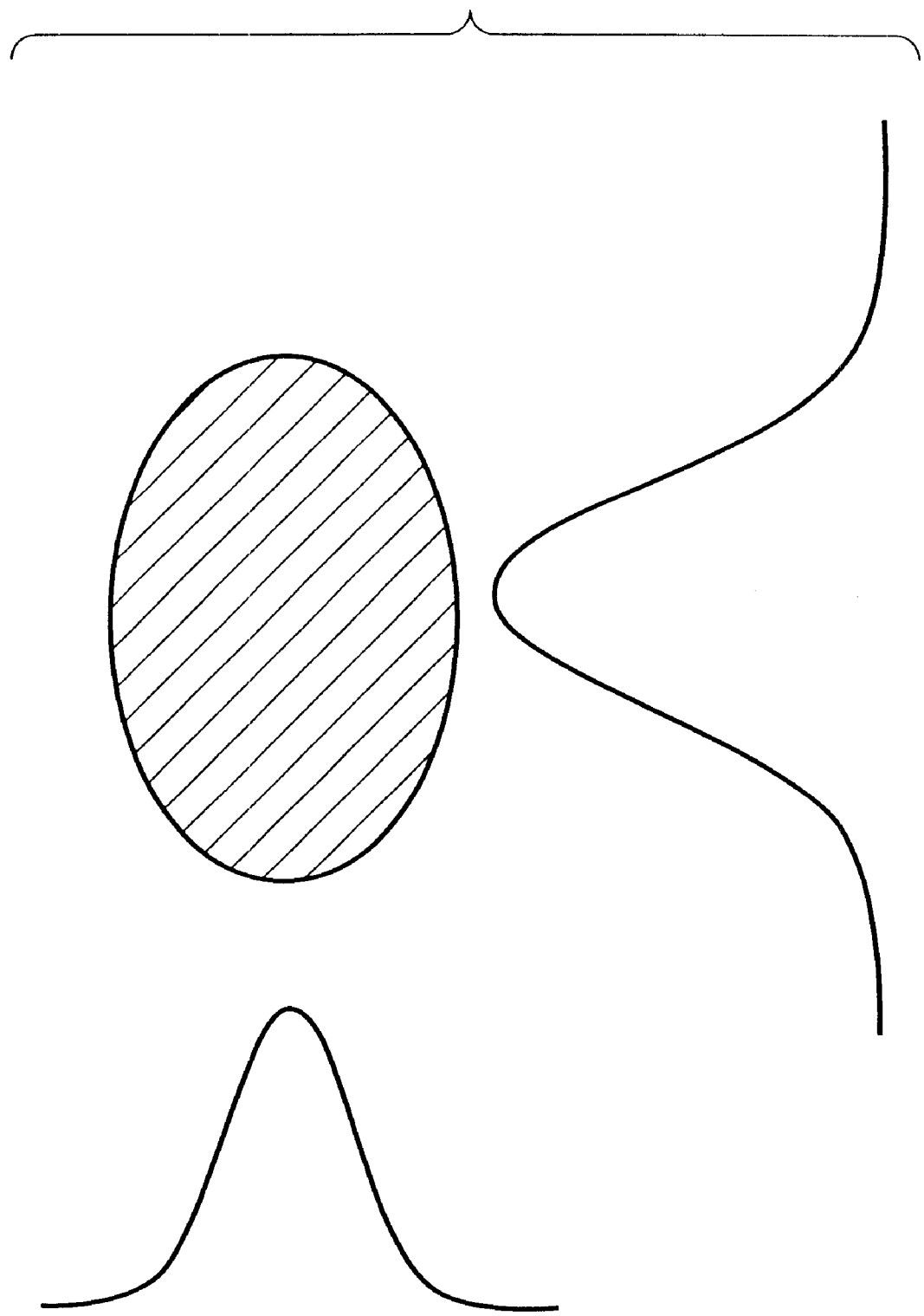
FIG. 25 is a graph showing the intensity distribution obtained in a case wherein a wafer to be inspected is not present in the foreign substance inspecting apparatus for detecting the height of a foreign substance according to the embodiment of the present invention.

FIG. 25 shows a signal output from a light-receiving portion obtained when no wafer is present. This signal output has a normal intensity distribution in both the vertical and horizontal directions. As a correction value for each pixel, the apparatus has a reciprocal of an output obtained when no wafer is present. Correction is performed by multiplying an output obtained when a wafer is actually loaded by this correction value. Even if the LD 14 has a normal intensity distribution, once correction is performed, a process identical to that performed when the LD 14 has a uniform distribution can be performed.

Figure 8:
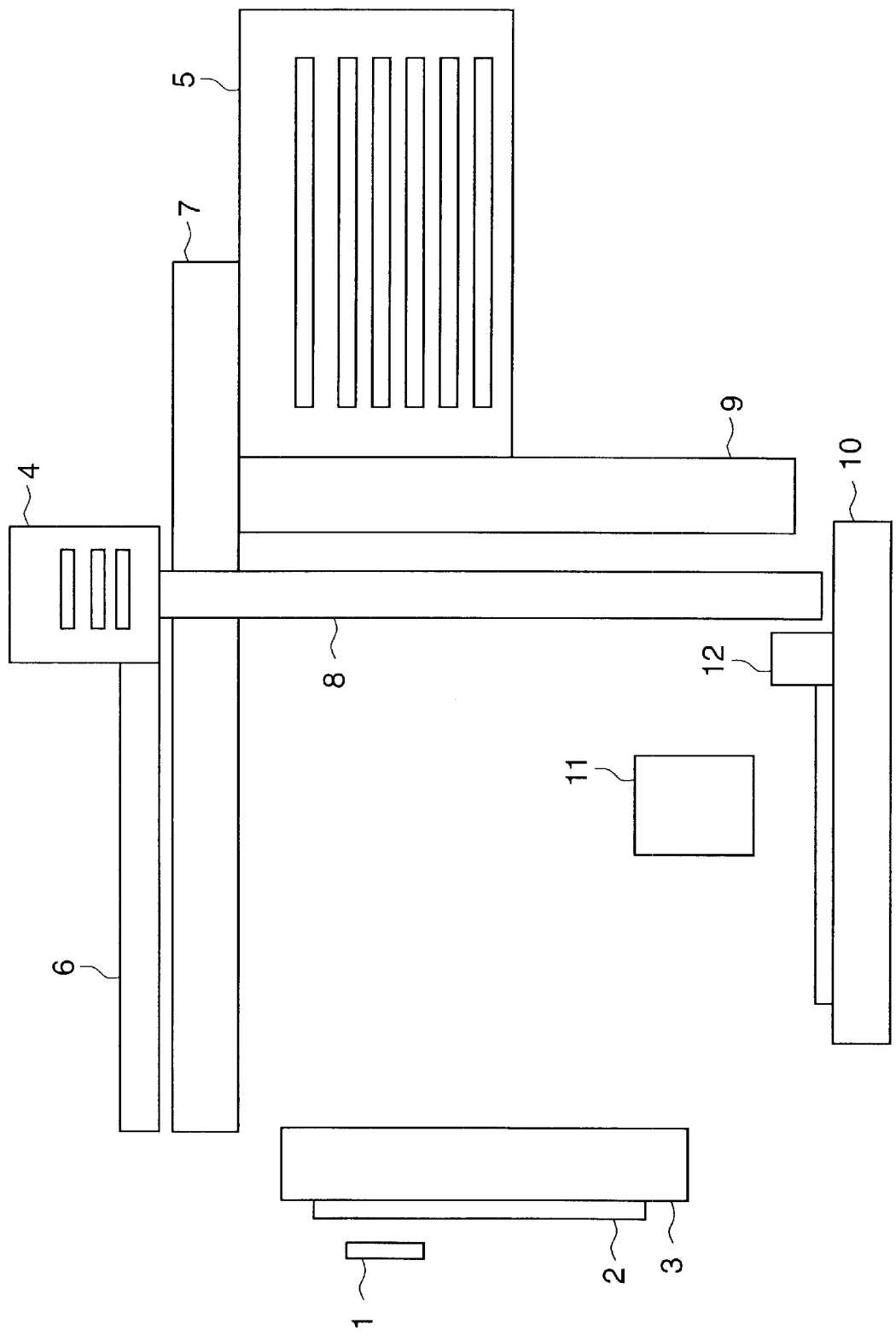
FIG. 8 shows an exposure apparatus incorporating foreign substance inspecting apparatuses for inspecting an X-ray mask and wafer, respectively.
Figure 9:
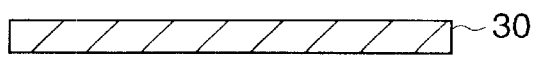
FIGS. 9 to 18 are views showing a conventional method of forming an X-ray mask.
Figure 10:
Figure 11:
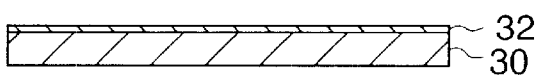
Figure 12:
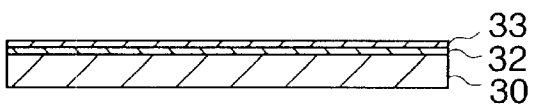
Figure 13:
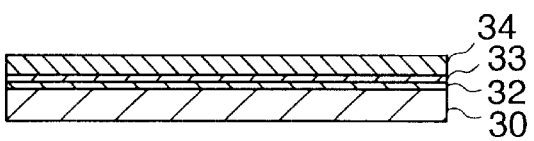
Figure 14:
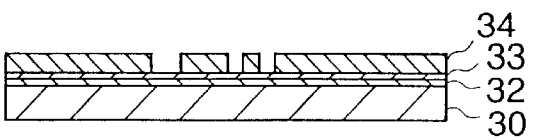
Figure 15:
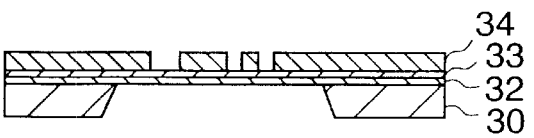
Figure 16:
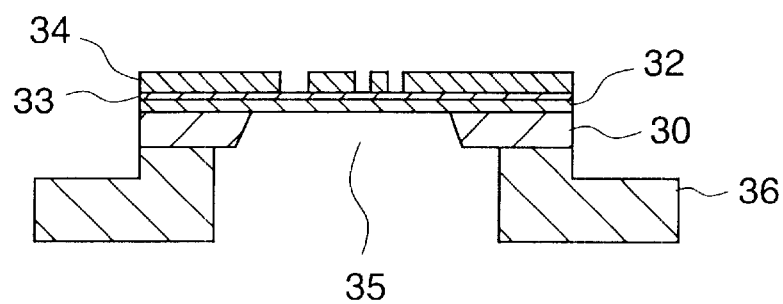
Figure 17:
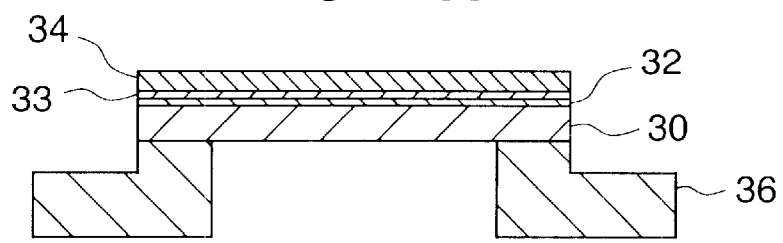
Figure 18:
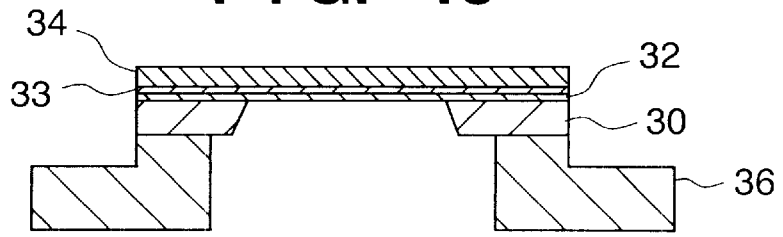
Figure 19:
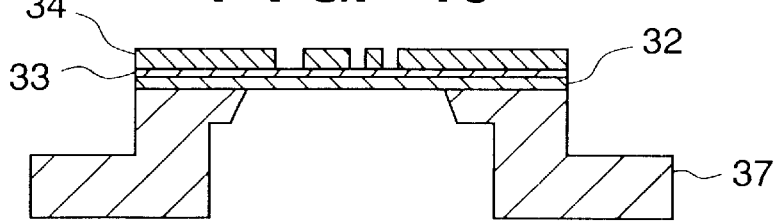
FIG. 19 is a view showing an arrangement in which a mask and frame are integrated.
Figure 20:
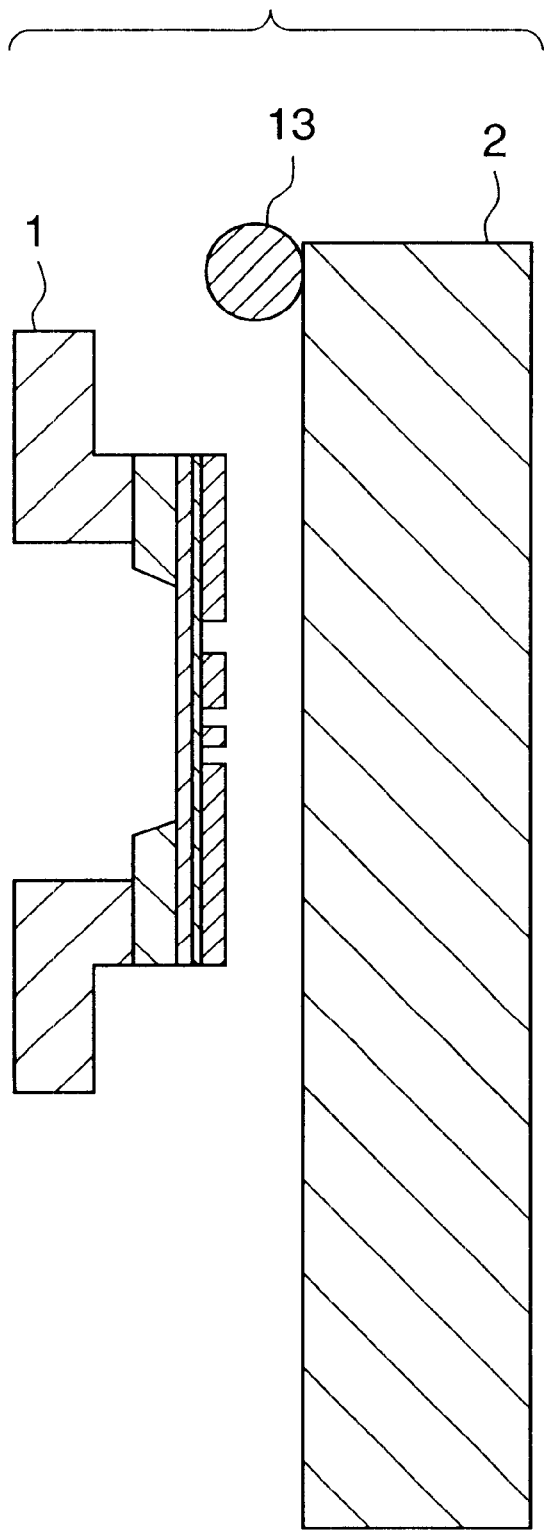
FIGS. 20 to 24 are views showing the flow as to how a foreign substance attaching to the periphery of a wafer moves to fracture a mask when the mask and wafer are set at a predetermined exposure gap.
Figure 21:
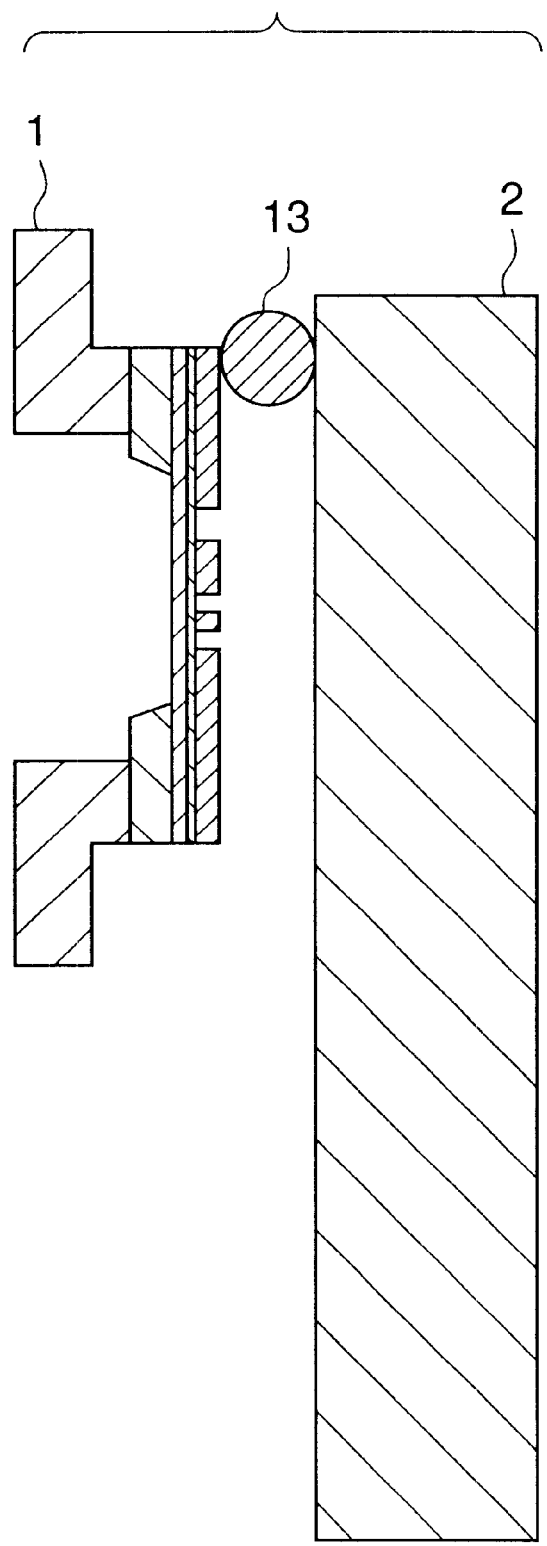
Figure 22:
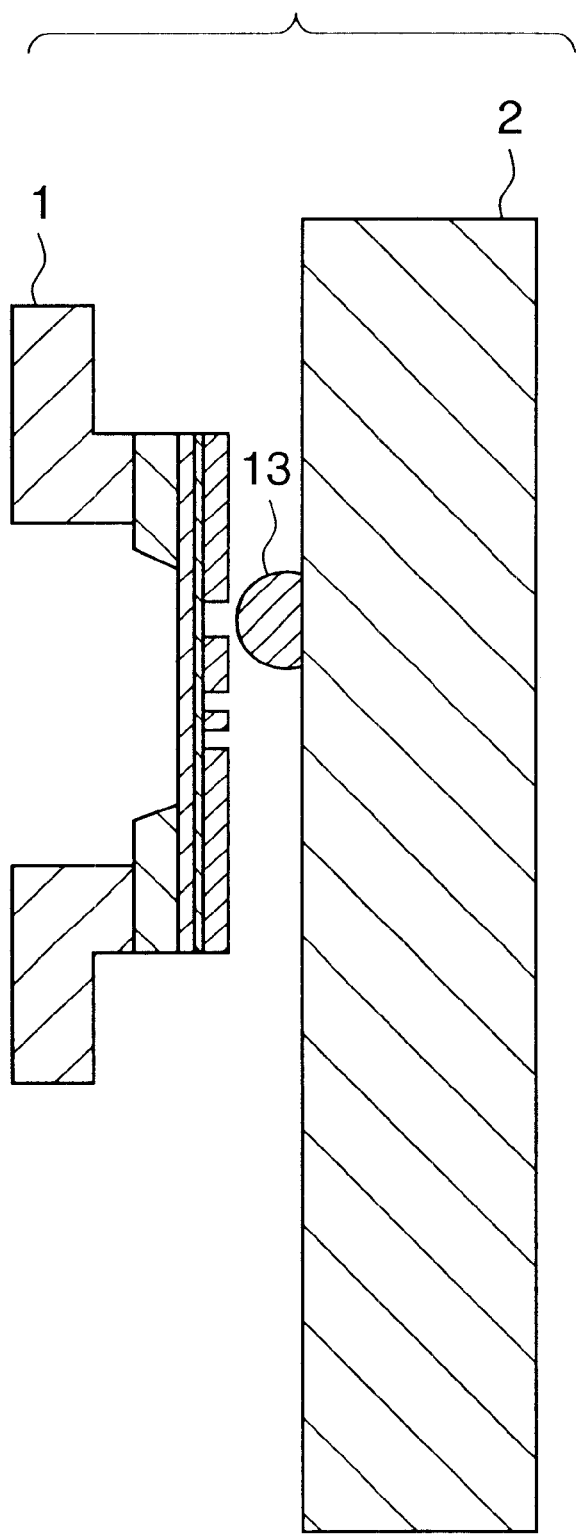
Figure 23:
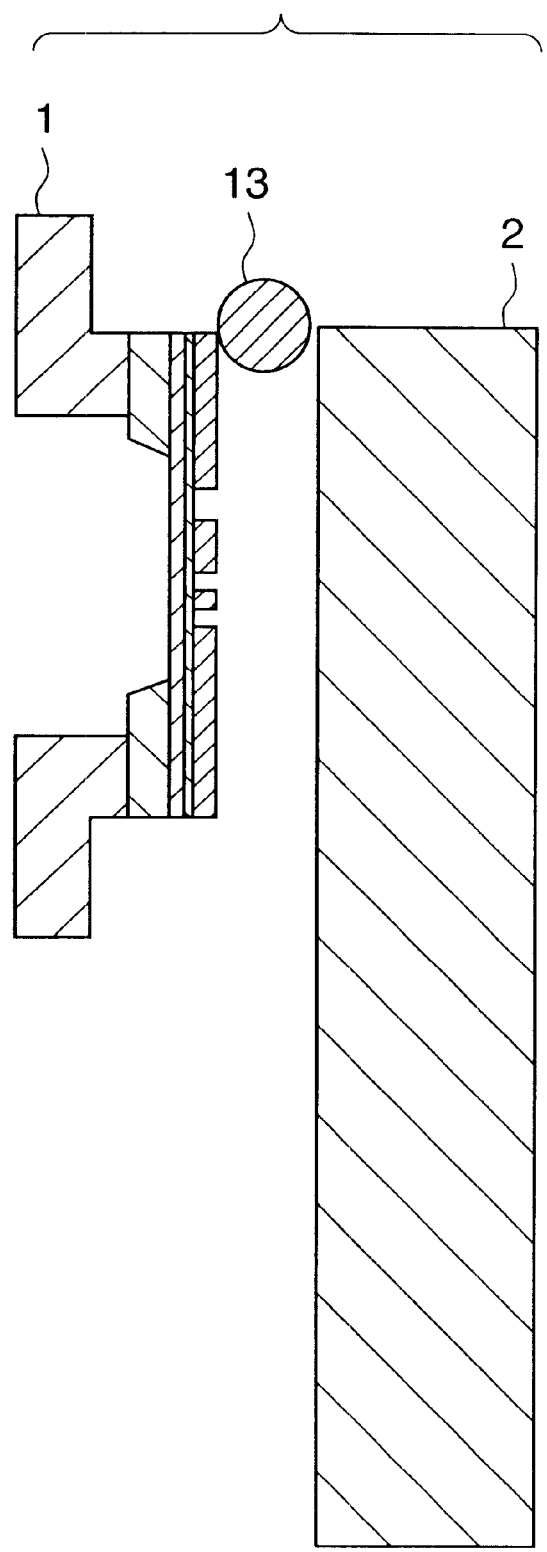
Figure 24:
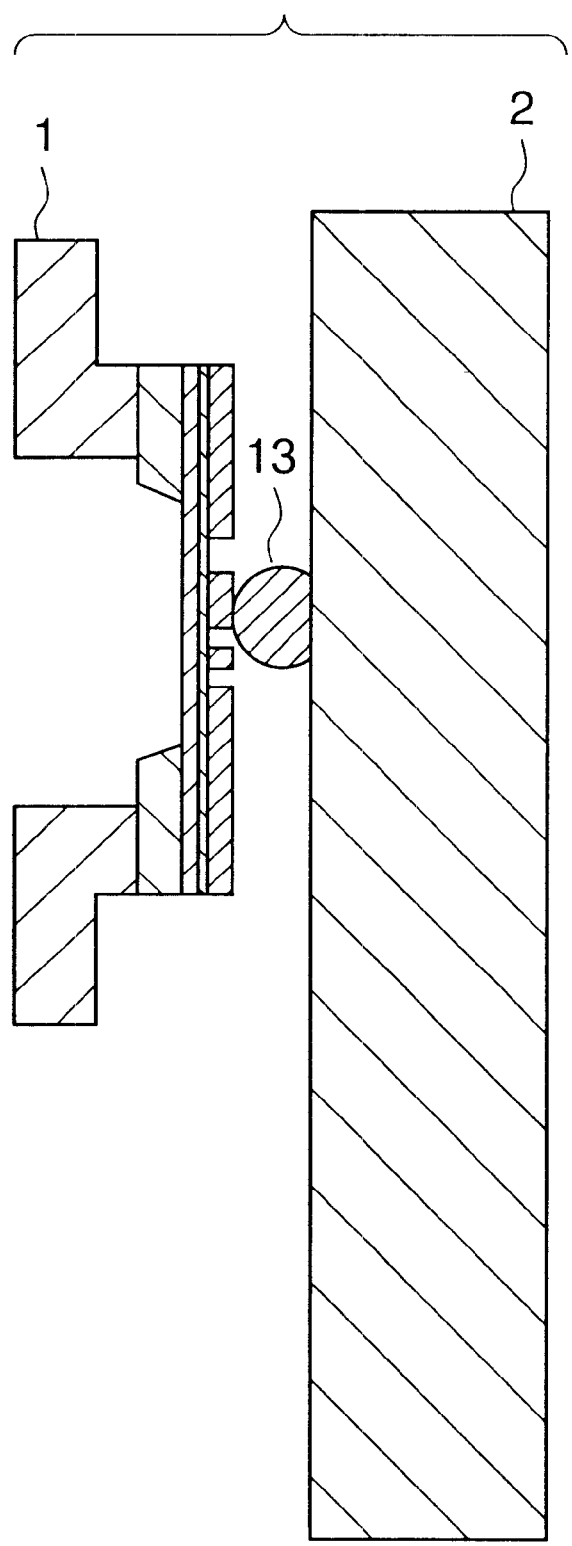

FIG. 8 shows an arrangement in which both a foreign substance inspecting apparatus, to which this detection principle that can also detect the height, and a conventional foreign substance inspecting apparatus, which determines the size of a foreign substance from a signal output, are arranged in a PXL exposure apparatus. In FIG. 8, a wafer 2 and mask 1 are vertically arranged in the exposure apparatus so that the wafer can be efficiently irradiated with X-rays with a wavelength of 7 Å to 10 Å horizontally emerging from the SR. The wafer 2 is exposed with an exposure gap of 10 μm to 30 μm with respect to the mask 1.

If the wafer and mask are not arranged vertically but are arranged horizontally, the X-rays must be bent at 90° with a mirror. As a mirror that can efficiently reflect the X-rays at 90° does not currently exist, the horizontal arrangement leads to a remarkably large loss in X-ray quantity.

Since the exposure range is 52 mm square at maximum, with a 300-mm wafer, exposure of 40 shots or more is performed while moving a vertical X-Y stage 3 which has an interferometer and on which the wafer is placed. Before being arranged upright at the exposure position, a plurality of masks and a plurality of wafers are arranged in clean-atmosphere boxes, respectively called a Standard Mechanical Interface (SMIF) 4 and a Front Open Unified Pod (FUOP) 5, and are accessed one by one when necessary with a mask transfer system 6 and wafer transfer system 7, and are transferred.

In FIG. 8, a mask transfer system 8 and wafer transfer system 9 are provided to perform foreign substance inspection for the mask and wafer. The transfer systems 6 and 7 described above can also respectively serve as the transfer systems 8 and 9.

The mask and wafer are placed on an X-Y stage 10 for foreign substance inspection by the transfer systems 8 and 9. The X-Y stage 10 is horizontal and does not require very high precision, different from the vertical wafer exposure X-Y stage 3 with the interferometer. The mask and wafer are arranged on the X-Y stage 10 such that their facing surfaces are located at an upper position, and are inspected by a foreign substance inspecting apparatus 11.

As the foreign substance inspecting apparatus 11, an existing oblique-incident foreign substance inspecting apparatus using polarization can be adopted. The foreign substance inspecting apparatus 11 has a detection system which determines the size of a foreign substance from the magnitude of the output, and inspects the entire surfaces of a wafer and mask excluding their peripheries.

A foreign substance inspecting apparatus 12 to be described next is a foreign substance detection system of this embodiment. When an exposure gap between the mask and wafer is set as a parameter, the foreign substance inspecting apparatus 12 discriminates the presence/absence of a foreign substance on the periphery of the wafer that can fracture the mask in accordance with the exposure gap by directly measuring the height of the foreign substance.

A mask and wafer inspected by the foreign substance inspecting apparatuses 11 and 12 and determined as having no foreign substance thereon are transported to the exposure position by the mask transfer system 6 and wafer transfer system 7, are rotated through 90° in the exposure apparatus, are arranged to stand upright, and are exposed.

The foreign substance inspecting apparatus 11 to which the existing foreign substance inspecting apparatus can be applied has a high speed with a short foreign substance measurement time of 1 minute or less when measuring the entire surface of an 8-inch wafer. Meanwhile, the foreign substance inspecting apparatus 12 for inspecting only the periphery of the wafer only takes a short inspection time of 10 seconds or less, since it can receive a signal by only rotating the wafer through one revolution at minimum. Therefore, most of the foreign substance inspection time required by this PXL exposure apparatus is the time required by the foreign substance inspecting apparatus 11, and does not decrease the throughput of the entire exposure.

As described above, according to this embodiment, inspection is performed by arranging both the foreign substance inspecting apparatus 11 with a detection method that determines the size of a foreign substance from the magnitude of a signal output, and the foreign substance inspecting apparatus 12 which detects the height of a foreign substance on only the periphery of the wafer. With this arrangement, a large-sized foreign substance on the periphery of the wafer that can fracture the mask can be detected without decreasing the entire throughput, and the object of the present invention is thus achieved.

In the embodiment shown in FIG. 8, both the foreign substance inspecting apparatus 11 with the detection method that determines the size of a foreign substance from the magnitude of a signal output, and the foreign substance inspecting apparatus 12 which can detect the height of a foreign substance are arranged in the PXL exposure apparatus. However, the embodiment of the present invention is not always limited to an exposure apparatus having two foreign substance detection systems. For example, the exposure apparatus may have a simple arrangement with only a foreign substance inspecting apparatus 12 which can detect the height of a foreign substance.

According to another embodiment, both a mask and wafer may be inspected by using so-called stand-alone foreign substance detection systems outside an exposure apparatus. The mask and wafer may then be transferred to the exposure apparatus under guaranteed cleanness, thereby achieving the same effect as that described above.

Regarding the relationship between the foreign substance detection systems and exposure apparatus, the foreign substance detection systems may not be stand-alone systems but may be so-called in-line systems that are connected to the exposure apparatus through a computer or the like. Alternatively, a wafer foreign substance detection system may be formed in a coater/developer which applies and develops a resist. When the foreign substance detection systems are arranged outside the exposure apparatus, the cleanness for transfer of the mask and wafer must be guaranteed after inspection, in the same manner as in the stand-alone arrangement.

Foreign substance inspection in the coater/developer may be performed before or after resist coating. What matters is where the foreign substance is located. If the location of the foreign substance cannot be identified, inspection may be performed both before and after resist coating.

Alternatively, an embodiment in which two foreign substance detection systems are not arranged in one apparatus may be adopted. Regarding a foreign substance that degrades the yield, stand-alone inspection may be performed with a foreign substance inspecting apparatus 11 with a detection method that determines the size of a foreign substance from the magnitude of a signal output while taking a sufficiently long period of time. A foreign substance inspecting apparatus 12 with the principle described in the above embodiment and capable of detecting the height of a foreign substance may be arranged in, e.g., a coater/developer or exposure apparatus, and the height of the foreign substance may be detected only on the periphery of a wafer with a high throughput.

If the location of the foreign substance is identified, it is most efficient to inspect the foreign substance immediately after it is identified. If the location of the foreign substance is not identified and inspection is to be performed not with a plurality of foreign substance detection units but with one foreign substance detection unit, the foreign substance detection unit may be arranged at the exposure position of the mask and wafer. With this arrangement, the cleanness after inspection need not be guaranteed, unlike in the case wherein the foreign substance detection systems are arranged as stand-alone systems.

If the foreign substance detection unit is arranged at the exposure position, it cannot perform exposure and inspection simultaneously, and accordingly, another problem of a decrease in throughput arises. As a countermeasure for this, a plurality of wafers may be arranged on the X-Y stage 3 with the interferometer shown in FIG. 8, and may be exposed and inspected simultaneously. Since the X-Y stage 3 with the interferometer is a high-precision stage that needs global alignment, it should not become large in size more than necessary so much that the cost will not increase.

As has been described above, according to the present invention, the height of a foreign substance on the periphery of a wafer can be measured. For example, the presence/absence of a foreign substance, which really poses an issue in PXL exposure, can be detected by discriminating this foreign substance from other foreign substances. Fracture of the mask is a specific matter in PXL exposure. Since the height of the foreign substance can be identified, the size of a foreign substance to be detected can be altered in accordance with the exposure gap between the mask and wafer as a parameter.

Therefore, a foreign substance with a size larger than the exposure gap or more can be prevented from entering between the mask and wafer to fracture the mask without erroneous detection, and highly reliable exposure can be performed.

The present invention is not limited to the above embodiments and various changes and modifications can be made within the spirit and scope of the present invention. Therefore, to apprise the public of the scope of the present invention the following claims are made.

What is claimed is:

1. A foreign substance inspecting method comprising the step of:

detecting a height of a foreign substance attaching to a periphery of a wafer by irradiating a light beam from a light source to the wafer, thereby detecting the presence/absence of a foreign substance with not less than a predetermined height, wherein the predetermined height is set to be substantially equal to a gap between the wafer and a mask at a wafer exposure.

2. The method according to claim 1, wherein the periphery of the wafer is irradiated with the light beam in a direction substantially tangent to an outer circumference of the wafer while rotating the wafer, thereby detecting the presence/absence of the foreign substance with not less than the predetermined height.

3. The method according to claim 2, wherein the light beam irradiating the periphery of the wafer is reflected by a reflecting member, is returned to an optical path the light beam has traveled, and is thereafter received, thereby the detecting presence/absence of the foreign substance with not less than the predetermined height.

4. A foreign substance inspecting method that is applied to an exposure apparatus, which exposes a mask and wafer separated from each other at a predetermined distance, said method comprising the step of:

detecting a height of a foreign substance attaching to the wafer by irradiating a light beam from a light source to the wafer, thereby detecting the presence/absence of a foreign substance with not less than a gap between the wafer and a mask at a wafer exposure.

5. A foreign substance inspecting method that is applied to an exposure apparatus, which exposes a mask and a wafer separated from each other at a predetermined distance, said method comprising the step of:

detecting a size and height of a foreign substance attaching to the wafer by irradiating a light beam from a light source to the wafer, thereby detecting the presence/absence of a foreign substance with not less than a gap between the wafer and a mask at a wafer exposure.

6. A foreign substance inspecting apparatus for inspecting a foreign substance attaching to a wafer, said apparatus comprising:

an irradiation unit for irradiating a periphery of the wafer with a light beam in a direction substantially tangent to an outer circumference of the wafer while rotating the wafer; and a detection unit for detecting the presence/absence of a foreign substance with not less than a predetermined height on the basis of the irradiating light beam, wherein the predetermined height is set to be substantially equal to a gap between the wafer and a mask at a wafer exposure.

7. The apparatus according to claim 6, further comprising a reflecting member for reflecting the light beam irradiating the periphery of the wafer, said reflecting member serving to return the irradiating light beam to an optical path the light beam has traveled, and said detection unit serving to receive the returned light, thereby detecting the presence/absence of the foreign substance with not less than the predetermined height.

8. An exposure apparatus for exposing a mask and a wafer separated from each other at a predetermined distance, said exposure apparatus comprising:

a foreign substance inspecting apparatus for inspecting a foreign substance attaching to a wafer, said inspecting apparatus having (i) an irradiation unit for irradiating a periphery of the wafer with a light beam in a direction substantially tangent to an outer circumference of the wafer while rotating the wafer, and (ii) a detection unit for detecting the presence/absence of a foreign substance with not less than a predetermined height on the basis of the irradiating light beam, wherein the predetermined height is set to be substantially equal to a gap between the wafer and a mask at a wafer exposure.

9. The exposure apparatus according to claim 8, wherein said foreign substance inspecting apparatus detects a foreign substance on the mask.

10. The exposure apparatus according to claim 9, wherein said foreign substance inspecting apparatus is provided in said exposure apparatus.

11. The exposure apparatus according to claim 10, wherein said foreign substance inspecting apparatus is provided at an exposure position of said exposure apparatus.

12. The exposure apparatus according to claim 8, further comprising a foreign substance inspecting apparatus for a patterned wafer.

13. The exposure apparatus according to claim 8, wherein said exposure apparatus is a proximity X-ray lithography exposure apparatus.

* * * * *